(12) United States Patent
Fisker

(10) Patent No.: US 10,602,992 B2
(45) Date of Patent: Mar. 31, 2020

(54) USING A CBCT BONE SCAN TO DESIGN A DENTAL ABUTMENT

(71) Applicant: 3SHAPE A/S, Copenhagen K (DK)

(72) Inventor: Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 379 days.

(21) Appl. No.: 15/538,819

(22) PCT Filed: Dec. 21, 2015

(86) PCT No.: PCT/EP2015/080773
§ 371 (c)(1),
(2) Date: Jun. 22, 2017

(87) PCT Pub. No.: WO2016/102451
PCT Pub. Date: Jun. 30, 2016

(65) Prior Publication Data
US 2018/0000569 A1    Jan. 4, 2018

(30) Foreign Application Priority Data

Dec. 22, 2014   (DK) .................. 2014 70816

(51) Int. Cl.
*G06F 17/50*      (2006.01)
*A61B 6/03*       (2006.01)
(Continued)

(52) U.S. Cl.
CPC ............... *A61B 6/032* (2013.01); *A61B 6/14* (2013.01); *A61B 6/4085* (2013.01); *A61C 8/005* (2013.01); *A61C 8/008* (2013.01); *G06F 17/5009* (2013.01)

(58) Field of Classification Search
CPC ..... A61C 13/0004; A61C 1/084; A61C 8/005; A61C 8/0068; A61C 8/0054; A61C 5/20;
(Continued)

(56) References Cited

U.S. PATENT DOCUMENTS

| 2008/0090207 A1 | 4/2008 | Rubbert |
| 2009/0042167 A1 | 2/2009 | Van Der Zel |

(Continued)

FOREIGN PATENT DOCUMENTS

| EP | 2 103 276 A1 | 9/2009 |
| WO | WO 2013/092744 A1 | 6/2013 |
| WO | 2014/064165 A1 | 5/2014 |

OTHER PUBLICATIONS

Office Action (Communication pursuant to Rule 164(2)(b) and Article 94(3) EPC) dated Jul. 19, 2018, by the European Patent Office in corresponding European Application No. 15 813 452.8-1126, (10 pages).
(Continued)

*Primary Examiner* — Kandasamy Thangavelu
(74) *Attorney, Agent, or Firm* — Buchanan Ingersoll & Rooney P.C.

(57) ABSTRACT

Disclosed is a method of creating a digital abutment design of a customized dental abutment, the including comprising: obtaining a bone scan comprising a digital representation of at least a part of a patient's jaw including the surface of the jawbone; and designing the digital abutment design of the customized dental abutment; wherein the design of the digital abutment design is at least partly based on fulfilling a set of predefined design criteria including the relationship between the digital representation of the jawbone and the digital abutment design.

14 Claims, 5 Drawing Sheets

(51) Int. Cl.
*A61C 8/00* (2006.01)
*A61B 6/14* (2006.01)
*A61B 6/00* (2006.01)

(58) Field of Classification Search
CPC . A61C 13/083; A61C 13/004; A61C 13/0022; A61B 19/44; A61B 6/032; A61K 6/0044; G06F 17/50; A61L 27/04
See application file for complete search history.

(56) References Cited

U.S. PATENT DOCUMENTS

| | | |
|---|---|---|
| 2010/0105009 A1 | 4/2010 | Karkar et al. |
| 2010/0105011 A1* | 4/2010 | Karkar ............ A61C 1/084 433/215 |
| 2010/0304334 A1* | 12/2010 | Layton ............ A61C 8/005 433/173 |
| 2011/0086328 A1 | 4/2011 | Wedeking |
| 2012/0003610 A1 | 1/2012 | Llop |
| 2012/0070802 A1 | 3/2012 | Woodward, III |
| 2012/0072178 A1 | 3/2012 | Beaudry et al. |
| 2012/0270179 A1* | 10/2012 | Holmstrom ............ A61C 8/005 433/173 |
| 2012/0295223 A1 | 11/2012 | Robb et al. |
| 2014/0032183 A1* | 1/2014 | Fisker ............ A61C 13/0004 703/1 |
| 2014/0234801 A1* | 8/2014 | Herrington ........ A61C 13/0004 433/202.1 |
| 2015/0025855 A1 | 1/2015 | Fisker et al. |
| 2015/0327958 A1* | 11/2015 | Llop et al. ......... A61C 13/0004 433/213 |

OTHER PUBLICATIONS

International Search Report (PCT/ISA/210) dated May 11, 2016, by the European Patent Office as the International Searching Authority for International Application No. PCT/EP2015/080773.

* cited by examiner

| 101 | Obtain a bone scan of the patient's jaw. |

| 102 | Determine the emergence profile of the adjacent teeth, and create a digital copy of the emergence profile. |

| 103 | Use the digital copy of the emergence profile as a design criteria, to create a digital abutment design with an emergence profile similar to the emergence profile of the adjacent teeth. |

| 104 | Design the part of the digital abutment which is above the margin line, based on predetermined design criteria. |

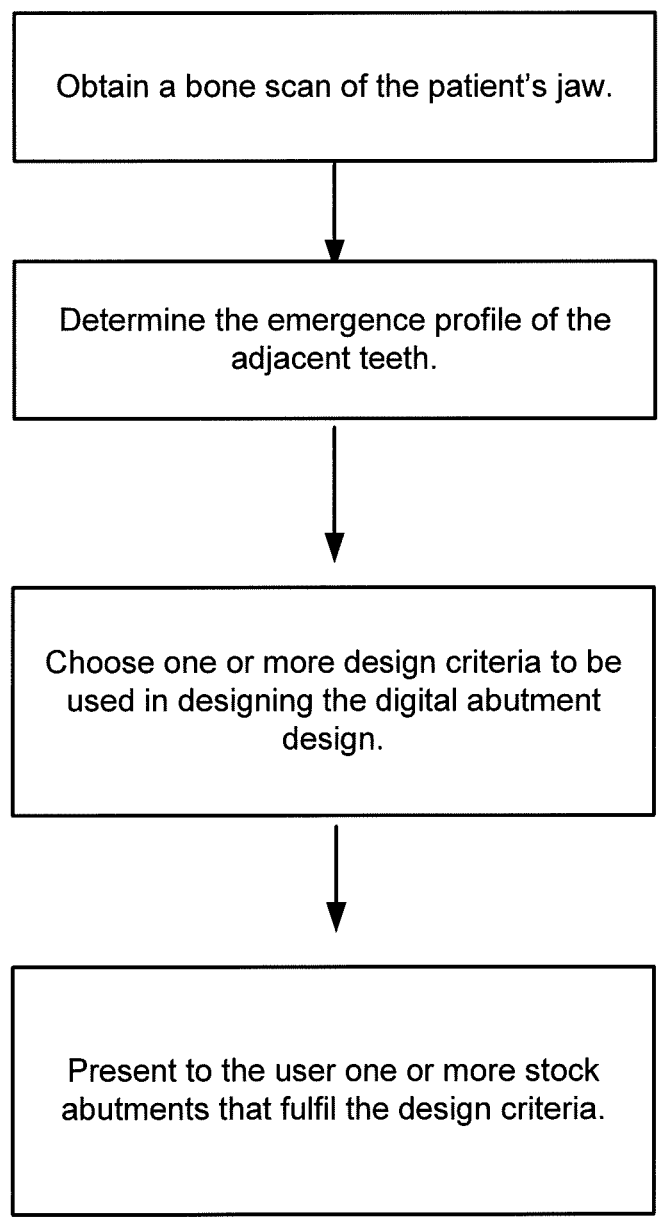

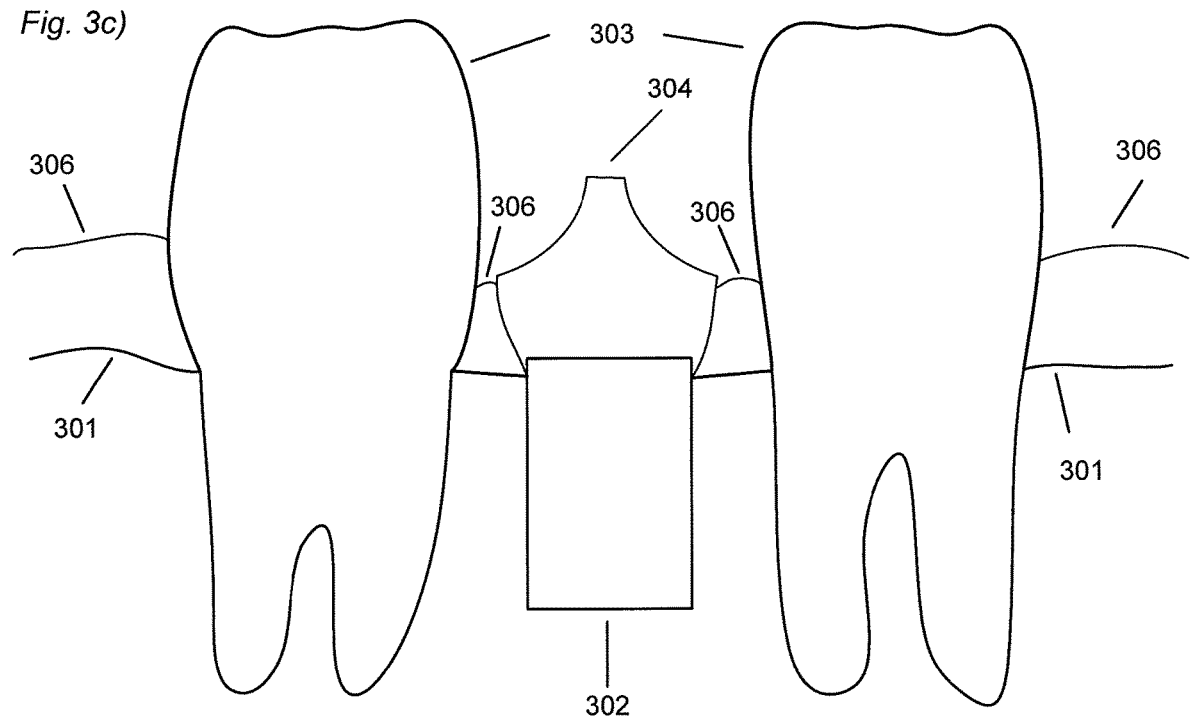

USING A CBCT BONE SCAN TO DESIGN A DENTAL ABUTMENT

FIELD OF THE INVENTION

This invention generally relates to designing or selecting an implant abutment. More particularly, the invention relates to using a bone scan of a patient's jaw to design an abutment based on predetermined design criteria.

Using the bone scan to constrain the design of the abutment while having a predetermined set of design criteria, will make it possible to design an abutment that will better fit a patient's specific situation.

BACKGROUND OF THE INVENTION

In the field of implant dentistry, it is known to use both cemented and screw retained restorations. A screw retained restoration has a screw access hole in the occlusal side, through which it is possible to fasten the restoration in the implant using a matching screw.

However, this method of attaching the restoration invariably means that the screw access hole has to be lined up perfectly with the direction of the implant borehole. In some situations, especially for anterior teeth, this arrangement will mean that the screw access hole would become an aesthetic liability.

One way to ameliorate this problem is to use an implant abutment and a cemented restoration. It is known in the field to use a CBCT scan to determine the position and shape of a dental implant.

However, it remains a problem to choose or design an abutment suited for each patient's specific situation.

SUMMARY

Disclosed is a method of creating a digital abutment design of a customized dental abutment, the method comprising:
  obtaining a bone scan comprising a digital representation of at least a part of a patient's jaw including the surface of the jawbone; and
  designing the digital design of the customized dental abutment;
  wherein the design of the digital abutment design is at least partly based on fulfilling a set of predefined design criteria comprising the relationship between the digital representation of the jawbone and the digital abutment design.

Consequently, the surface of the patient's jawbone is known from the bone scan, and this information can be used to optimize the design of the abutment, in order to achieve for example a functional and/or aesthetic final result. The bone scan may also show the placement of any dental implants in the jaw of the patient, and the abutment may be designed in order to fit this already existing implant. Furthermore, the bone scan may show the surface of the teeth surrounding the implant site, giving information about for example the emergence profile of the adjacent teeth.

It is also possible to design the restoration to fit the surrounding dentition, and designing the abutment to fit both the implant as well as allowing for the designed restoration to fit the abutment.

The bone scan can be any type of scan that is capable of showing the surface of the jawbone and any remaining teeth in the patient. This can for example be a dental x-ray, CT scan, PET scan or a cone beam CT (CBCT) scan. In some embodiments the bone scan is a CBCT scan.

The CBCT scan will give a higher resolution in the final digital model of the patient's bone structure than a conventional x-ray.

In some embodiments, the relationship between the digital representation of the jawbone and the digital abutment design comprises the relationship between the surface of the digital representation of the jawbone and the outer surface of the digital abutment design. The surface of the jawbone is determined from the bone scan. It is therefore possible to define the relationship using for example a vector representation in the design environment.

In some embodiments the voxel data of the CBCT scan is segmented to provide an image of the surface of the patient's jawbone. Segmentation can be done using a number of well-known techniques such as voxel based segmentation, region-based segmentation, edge-based segmentation, model based segmentation, deformable models, point distribution models, Markov random fields, Atlas-guidance, or any other segmentation technique. Where the original CBCT scan is a 3D voxel representation, the segmented scan is a 3D surface representation, where the surface is for example a mesh representation.

Using the segmented surface image takes less computer hardware resources to manipulate. A number of different digital tools already exist which use surface representations obtained from surface scans, and these digital tools can then be adapted to work with the segmented surface representation from the CBCT scan. Also, the surface image more closely resembles a classical x-ray image, which some dentists may prefer.

In some embodiments, the predetermined design criteria comprises the emergence profile of the digital abutment design. In order to achieve an aesthetically pleasing and functional final look, it is preferred that the emergence profile of the abutment is made to conform to the surrounding dentition. In some embodiments this is achieved by including data about the tooth or teeth adjacent to the implant site in the bone scan. The adjacent teeth may be either the patient's original teeth or any type of restoration including implant restorations. The ability of the abutment and corresponding restoration to conform to the anatomy and existing tissue volume enables the creation of the desired interproximal papilla and final gingival profile. When using data about the emergence profile of the adjacent teeth, the abutment can be designed to have a similar emergence profile, thereby conforming to the contours of the natural tooth, so that there can be a seamless transition to the restoration.

Of course, the emergence profile of the digital abutment design may differ depending on the preferences of the user performing the design, but a good starting point is to use the emergence profile of the existing teeth.

In some embodiments in order to determine the subgingival emergence profile of the adjacent teeth, it is necessary to make use of a bone scan, since the subgingival emergence profile is not visible in a surface scan. It has not previously been possible to take the sub-gingival emergence profile of the adjacent teeth into account when creating the digital abutment design, because only a surface scan has been taken into consideration, or the abutment has been designed in a manual process using a physical model. The physical model has typically been a gypsum model, made from an impression taken of the patients teeth. Therefore, the physical model only has information about the surface structure of the teeth above the gingiva, and contains no information about the sub-gingival emergence profile of the teeth.

In order to emulate the emergence profile of the adjacent teeth in the digital design of the abutment, the emergence profile of the adjacent teeth is determined. A digital representation of the emergence profile is generated, and this is then copied to the digital design of the abutment, to create a similar emergence profile for the abutment.

In some embodiments, the predetermined design criteria may comprise the prep length of the abutment. From the bone scan, the total length of the adjacent teeth can also be determined. For the proper retention and resistance form of the final restoration, it is important that the prep length of the abutment should be designed to have a minimum length of at least 3 or 4 mm. Once the emergence profile of the abutment has been designed, it is possible to test whether a prep length of at least 3 or 4 mm is possible, while keeping the final restoration having a substantially similar length as the adjacent teeth. If it is not possible to design the abutment with a prep length of at least 3 or 4 mm, the emergence profile should preferably be redesigned. Alternatively, the determination can be made that a screw retained restoration is the best option.

In some embodiments, the predetermined design criteria may comprise the position of the margin line. When determining the position of the margin line of the abutment/restoration interface, the thickness of the gingiva should be taken into account. This is due to the fact that the margin line of the abutment should not be too close to the gingiva surface. One way to accomplish this, is to set a design criterion to be the position of the margin line relative to both the gingiva surface and the jawbone surface. For example, the relative distance could be set to be a fraction of the distance from the surface of the jawbone to the surface of the gingiva no more than 0.1, 0.2, 0.3, 0.4, 0.5, 0.6, 0.7, 0.8 or 0.9 times the distance from the surface of the jawbone to the surface of the gingiva.

In some embodiments, the predetermined design criteria may comprise the depth of the margin line below the surface of the gingiva. For a functional final result of any planned restoration, it should be possible to remove any excess cement after the final seating of the restoration. Therefore, the margin line of the abutment/restoration interface should not be situated too deeply below the gingival surface level. Therefore, the margin line should be placed no deeper than 1.5 mm below the gingival margin. More preferably, for a metal or titanium abutment, margin depths of 0.5 mm on the lingual, 1 mm on the mesial and distal region, and 1.5 mm on the facial side provides adequate access to the margins for cleaning out any excess cement, and to hide the abutment/restoration junction.

In order for the abutment to be able to retain the restoration, it is important that there is an adequate inter-occlusal clearance. In some embodiments, the inter-occlusal distance is determined by measuring the distance between the implant fixture surface and the opposing dentition in the bone scan. This can be done by standard methods in the design environment. In order to prevent the final restoration from dislodging from the abutment, this distance should be no less than 5 mm, in order to give sufficient space for the abutment margin, adequate resistance form and thickness of the restoration. If the distance between the implant fixture surface and the opposing dentition is determined to be less than 5 mm, then a screw retained restoration should be chosen instead of an abutment with cemented crown. In this case the screw retained restoration would be able to allow the proper thickness of ceramic on the restoration.

In some embodiments, the predetermined design criteria may comprise a facial tissue thickness of at least 2 mm. The aesthetics of a final restoration is particularly important for the anterior teeth, as these are the most visible. If the tissue thickness on the facial side of the abutment is less than 2 mm, a titanium or metal abutment may show through the gingival tissue. Therefore, if the bone scan shows that the implant position is facial to the adjacent teeth or the surface scan shows that the implant position is less than 3 mm below the gingival margin, a zirconia abutment should be considered. This is particularly important if the cervical of the patients teeth are visible when the patient smiles, in order to minimize shadowing apical to the gingival margin seen with titanium abutments.

The software for designing the digital abutment design may be presented to the user as a design environment in a graphical user interface (GUI). The GUI can be configured to display a bone scan image of at least a part of a patient's jaw including the surface of the jawbone, and have controls for manipulating the design of digital dental abutment. There may also be an indicator configured to indicate, or give a warning, when one or more of the predefined design criteria are not met. For example, the predetermined design criteria may be set as threshold values, and when the threshold values are violated, a warning may be displayed.

In particular, disclosed herein is a method selecting a dental abutment from a digital library of stock dental abutments, the method comprising:

obtaining a bone scan comprising a digital representation of at least a part of a patient's jaw including the surface of the jawbone;

choosing the digital stock abutment that best fulfils a set of predetermined design criteria based on a weighted algorithm of the design criteria.

A dental laboratory often has access to one or more libraries of stock abutments. These are often available as digital models in the design environment. Applying one or more of the design criteria, the design environment can suggest one or more stock abutments available to the technician that fulfil the design criteria. If no stock abutments available to the technician fulfil all the design criteria, the design environment can suggest which stock abutment would provide the least problems, or suggest using a customized abutment instead. Determining the most appropriate stock abutment, can be done using a weighted algorithm of the design criteria.

Further predetermined design criteria may comprise:

a lingual margin depth of at least 0.5 mm, and/or a mesial and/or distal margin depth of at least 1 mm, and/or a facial margin depth of at least 1.5.

alllowing for a final gingiva thickness of at least 2 mm on the facial side of the abutment.

a minimum abutment prep length of 3 mm.

an appropriate path of insertion for a final restoration.

Some embodiments may comprise a computer program product comprising program code means configured to cause a computer to perform the steps of the method according to any of the embodiments of this specification when the computer executes said program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 1 shows a flowchart of the method according to an embodiment of the invention.

FIG. 2 shows a flowchart of the method according to another embodiment of the invention.

FIG. 3a-c shows a visualisation of the method according to an embodiment of the invention.

DETAILED DESCRIPTION

Figure 3A:
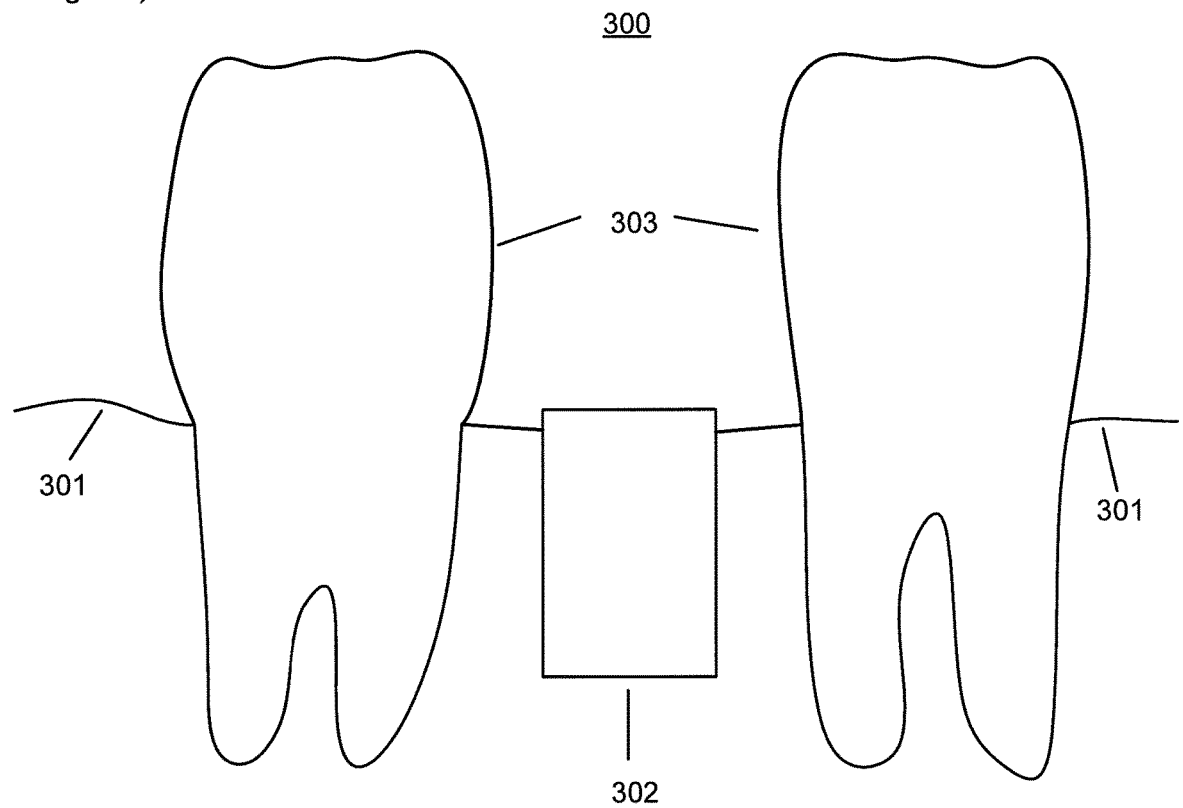

In the following description, reference is made to the accompanying figures, which show by way of illustration how the invention may be practiced.

FIG. 1 shows an example of a method 100 according to an embodiment of the invention. In step 101, a bone scan of the patient's jaw is obtained. The scan may comprise a dental implant already fixed in the patient's jawbone. Obtaining the scan may involve the physical operation of a machine, and performing the scan on the patient. Obtaining may also mean loading a previously acquired scan into a computer. In step 102 the emergence profile(s) of the tooth or teeth adjacent to the site of the wanted abutment are determined, and a digital data representation of this emergence profile is generated. In step 103 the digital abutment design is created, using the digital data representation of the emergence profile of the adjacent teeth, so that the digital abutment design is designed with a substantially similar emergence profile. The emergence profile is the part of the digital abutment design that is above the level of the jawbone or implant, up to the margin line on the digital abutment design. In step 104 the upper portion of the digital abutment design is designed. The upper portion should have a length of at least 3 mm in order to facilitate retention of the final restoration on the abutment. The upper portion of the digital abutment design may also be angled relative to the surface of the jawbone. This is done in order to have a viable path of insertion of the final restoration, taking into account the shape and position of the neighbouring teeth. The shape and position of the neighbouring teeth is also determined from the bone scan.

FIG. 2 shows an example of the method 200 according to another embodiment of the invention. In step 201, a bone scan of the patient's jaw is obtained. The scan may comprise a dental implant already fixed in the patient's jawbone. Obtaining the scan may involve the physical operation of a machine, and performing the scan on the patient. Obtaining may also mean loading a previously acquired scan into a computer. In step 202 the emergence profile(s) of the tooth or teeth adjacent to the site of the wanted abutment are determined, and a digital data representation of the emergence profile is generated. In step 203, the user may define a set of design criteria to be used in selecting a digital abutment design. The design software may already have default design criteria, that are used unless changed by the user. In step 204, the design software checks one or more stock abutment libraries that are available in digital form. A check is performed for each available abutment, to see if all predetermined design criteria are fulfilled. If one or more stock abutments fulfil all the predetermined design criteria, these possible abutments are shown to the user, who may then select the abutment of his/her choice. Alternatively, if none of the stock abutments available to the user fulfil all criteria, an error message may be shown, and the user may be prompted to design a customized abutment instead, for example using the method described in FIG. 1. In another alternative, the stock abutment which most closely fulfils the design criteria may be presented to the user, possibly with a warning describing which of the design criteria are not fulfilled.

FIG. 3a shows a bone scan 300 as disclosed herein. The bone scan 300 shows the surface of the jawbone 301, a dental implant 302 where no abutment has yet been designed or chosen, and any remaining teeth 303 adjacent to the implant position. The emergence profile of the adjacent teeth can be determined from this image. Dental implants from different manufacturers may have different attachment profiles, and the digital abutment design should be designed to fit the dental implant 302 in the patient's jaw.

Figure 3B:
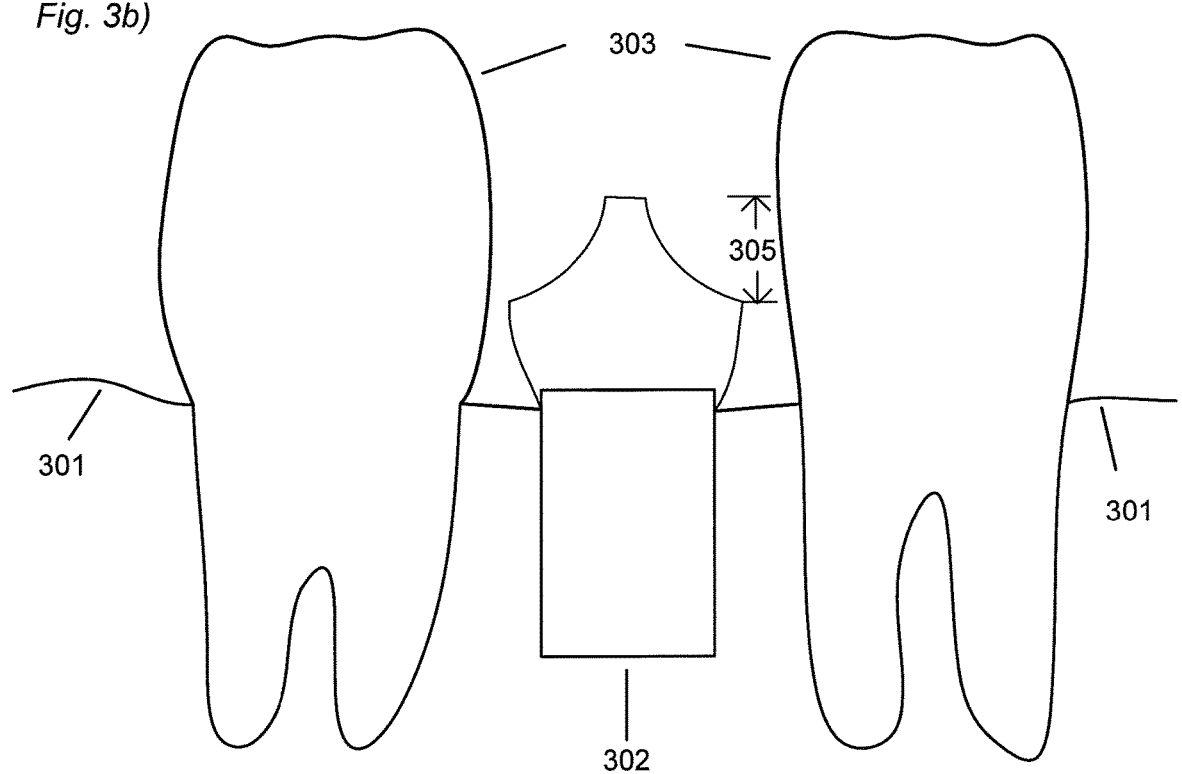

FIG. 3b shows the same view as FIG. 3a, now comprising an abutment 304 designed according to predetermined design criteria. The abutment 304 is in this example designed to emulate the emergence profile of the adjacent teeth. The left side of the abutment 304 is designed to emulate the left side of the emergence profile of the tooth adjacent to the left of the abutment 304, and the right side of the abutment 304 is designed to emulate the emergence profile of the right side of the adjacent tooth to the right side of the abutment 304. The prep length 305 should be designed to be at is at least 3 mm for proper retention and resistance of the final restoration.

In FIG. 3c, a surface scan showing the surface contour 306 of the gingiva is added. The surface scan may also comprise information about the surface of the teeth. The surface scan may be obtained by for example scanning a physical impression taken of the patient's teeth and gums or a gypsum model of the patient's teeth or gums using a desktop scanner, for example the D900 by 3Shape. The surface scan may also be obtained by using an intraoral scanner, such as the TRIOS by 3Shape. The surface scan gives information about the surface level of the gingiva 306.

Although FIGS. 3a-3c have shown an embodiment of the invention wherein the abutment to be designed is for a molar, the invention may equally be practiced on premolars, canines or incisors.

The predetermined design criteria may also comprise a lingual margin depth of no more than 0.5 mm, a mesial and distal margin depth of no more than 1 mm, and a facial margin depth of no more than 1.5 mm. If the margin line is placed deeper than this with respect to the surface of the gingiva, it will become difficult to remove any excess cement from the patient's mouth once the restoration has been placed on the final abutment.

It should also be noted that the shape of the abutment can be used to define an appropriate path of insertion of the final restoration. Normally, this design parameter would be determined based on a surface scan. However, using the disclosure of this invention, it is possible to design the customized abutment to define an appropriate path of insertion of the final restoration using only the bone scan, since the surface of both the jawbone and the adjacent teeth is visible in the bone scan.

Futhermore, although FIGS. 3a-3c shows a situation where the prepared tooth is a molar, the described workflow would also work the same way for pre-molars, canines etc.

Figure 4:
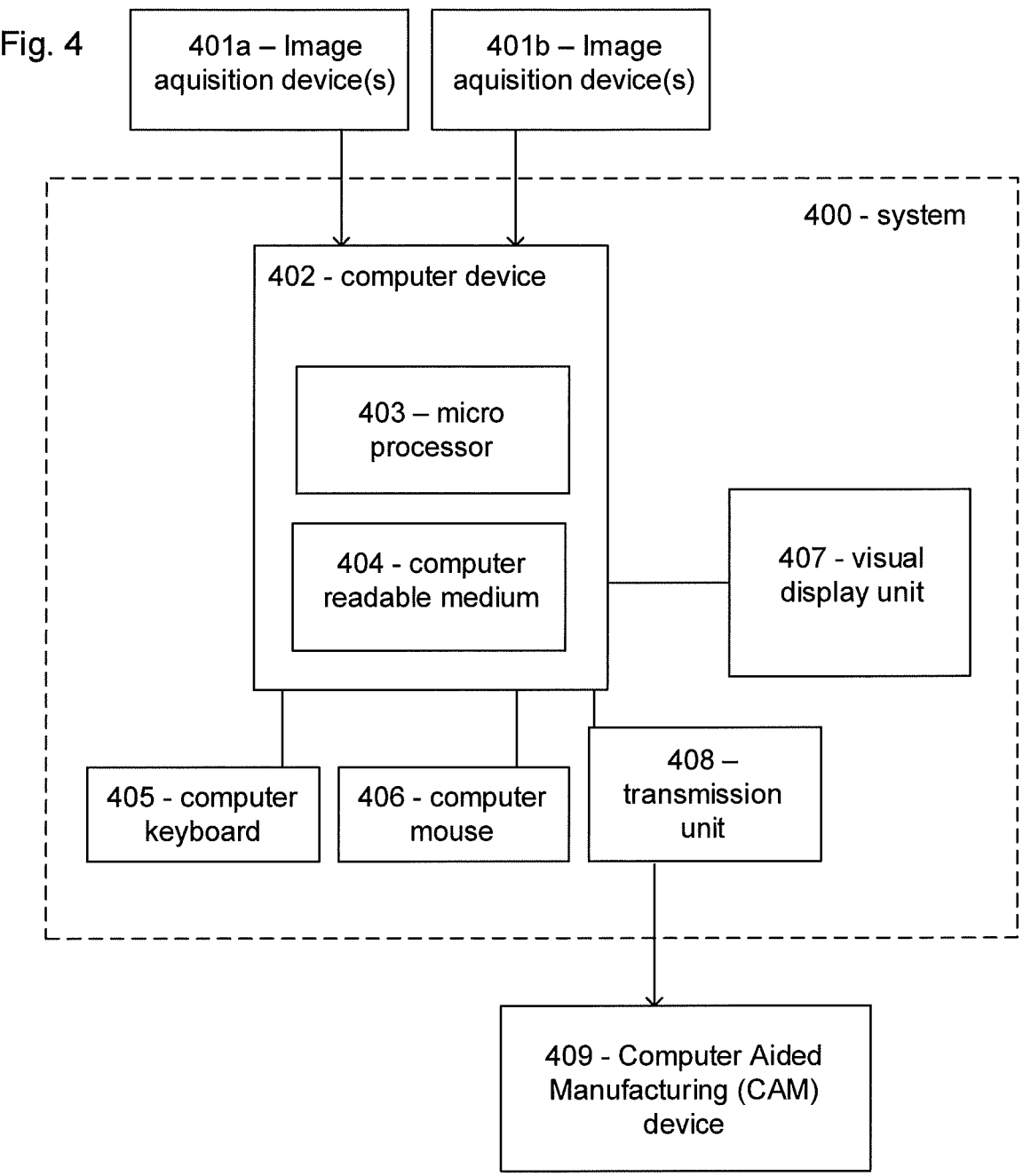
FIG. 4 shows a schematic representation of a system according to embodiments of the invention.

FIG. 4 shows a schematic of a system according to an embodiment of the invention. The system 400 comprises a computer device 402 comprising a computer readable medium 404 and a microprocessor 403. The system further comprises a visual display unit 407, a computer keyboard 405 and a computer mouse 406 for entering data and activating virtual buttons visualized on the visual display unit 407. The visual display unit 407 may for example be a computer screen.

The computer device 402 is capable of obtaining digital representations of at least a part of a patient's jaw including the surface of the jawbone from e.g. a CBCT scanner 401a.

The obtained digital representations can be stored in the computer readable medium 404 and provided to the processor 403.

The computer device 402 is further capable of receiving a digital 3D representation of the surfaces of the patient's set of teeth and gingiva from a image acquisition device 401b, for example a 3D scanning device, such as the TRIOS intra-oral scanner manufactured by 3shape TRIOS NS, or capable of receiving scan data from such a 3D scanning device and forming a digital 3D representation of the patient's set of teeth and/or gingiva based on such scan data. The received or formed digital 3D representation can be stored in the computer readable medium 404 and provided to the microprocessor 403.

The system 400 is configured for allowing an operator to design a customized dental abutment using information obtained from the bone scan and/or the surface scan, with limits being set based on pre-determined design criteria. This can be realized for example by displaying the digital representation of the patient's jaw on the visual display unit 407, and the operator can then visualize his/her abutment design on the visual display unit, with respect to the surface of the patient's jaw.

The system comprises a unit 408 for transmitting the digital designs of the customized dental abutment to e.g. a computer aided manufacturing (CAM) device 409 for manufacturing the customized dental abutments or to another computer system e.g. located at a milling center where the customized dental abutments are manufactured. The unit for transmitting can be a wired or a wireless connection, and the transmission may be done for example using the internet or File Transfer Protocol (FTP).

The 3D scanning of the patient's set of teeth and/or gingiva using the 3D scanning device 401b, and/or the bone scan using the CBCT scanner 401b can be performed at a dentist while the designing of the customized dental abutment is performed at a dental laboratory. In such cases the digital 3D representation of the patient's set of teeth and/or the 3D representation of the patient's jaw acquired from the CBCT scanner can be provided via an internet connection between the dentist and the dental laboratory.

The system 400 as shown is an illustrative example. For example, the computer device 402 may comprise more than one micro processor 403 and/or more than one computer readable medium 404, the visual display unit 407 may be integrated in the computer device 402 or be separate from the computer device 402, etc.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method of generating a digital abutment design of a customized dental abutment, wherein the method comprises:
   obtaining a bone scan of a jawbone comprising a digital representation of at least a part of a patient's jaw including a surface of the jawbone; and
   generating the digital abutment design of the customized dental abutment;
   where the digital abutment design is at least partly based on fulfilling a set of predefined design criteria comprising a relationship between the digital representation of the surface of the jawbone and the digital abutment design,
   wherein the bone scan comprises a Cone Beam Computed Tomography (CBCT) scan,
   the method further comprising:
   segmenting the voxel data of the CBCT scan to provide at least a digital bone surface representation; and
   using the digital bone surface representation to constrain the digital design of the customized dental abutment to confirm that the predefined design criteria have been fulfilled.

2. The method according to claim 1, wherein the relationship between the digital representation of the surface of the jawbone and the digital abutment design comprises the relationship between the surface of the digital representation of the jawbone and the outer surface of the digital abutment design.

3. The method according to claim 1, wherein the bone scan further comprises information about the shape and position of at least part of one or more teeth adjacent to a desired abutment position.

4. The method according to claim 1, wherein the predetermined design criteria comprises making an emergence profile of the abutment conform to an emergence profile of sub-gingival part of the at least one neighbouring existing tooth.

5. The method according to claim 4, wherein the emergence profile of the neighbouring tooth is determined and digitally copied, and the digital copy is used to design the emergence profile of the abutment.

6. The method according to claim 1, the method further comprising:
   obtaining a surface scan of at least a part of the patient's jaw, comprising at least part of a surface of surrounding gingiva; and
   placing a margin line of the abutment at a predetermined position relative to the surface of the surrounding gingiva and the surface of the jawbone.

7. The method according to claim 1, wherein the path of insertion of a final restoration is determined using only the bone scan.

8. A system for designing a customized dental abutment, the system comprising:
- a computer device, the computer device comprising:
- at least one microprocessor;
- at least one computer readable medium storing computer executable instructions which when executed by the microprocessor, execute the method of generating a digital abutment design of the customized dental abutment of claim 1;
- a visual display unit;
- a computer keyboard and a computer mouse; and
- a transmission unit for transmitting the customized dental abutment design from the system to a computer aided manufacturing device.

9. The method according to claim 1 wherein the predefined design criteria comprise threshold values that generate a warning when violated.

10. A method of generating a digital abutment design of a customized dental abutment, wherein the method comprises:
- obtaining a bone scan of a jawbone comprising a digital representation of at least a part of a patient's jaw including a surface of the jawbone; and
- generating the digital abutment design of the customized dental abutment;
- where the digital abutment design is at least partly based on fulfilling a set of predefined design criteria comprising a relationship between the digital representation of the surface of the jawbone and the digital abutment design,
- wherein the predefined design criteria comprise threshold values that generate a warning when violated.

11. A method of selecting a dental abutment from a digital library of stock dental abutments, the method comprising:
- obtaining a bone scan of a jawbone comprising a digital representation of at least a part of a patient's jaw including a surface of the jawbone;
- choosing the digital stock abutment that best fulfils a set of predetermined design criteria based on a weighted algorithm of the design criteria.

12. The method according claim 11, wherein the bone scan further comprises information about the shape and position of at least part of one or more teeth adjacent to a desired abutment position.

13. The method according to claim 11, wherein the predetermined design criteria comprises choosing the stock abutment so that the emergence profile of the stock abutment conforms to an emergence profile of the sub-gingival part of the at least one neighbouring existing tooth.

14. The method according to claim 11, wherein the path of insertion of a final restoration is determined using only the bone scan.

* * * * *